United States Patent
Mori et al.

(10) Patent No.: US 7,164,054 B2
(45) Date of Patent: Jan. 16, 2007

(54) LINER FOR PATCH

(75) Inventors: Yoshiaki Mori, Toyama (JP); Haruo Saito, Toyama (JP)

(73) Assignee: Lead Chemical Co., Ltd., Toyama (JP)

( * ) Notice: Subject to any disclaimer, the term of this patent is extended or adjusted under 35 U.S.C. 154(b) by 0 days.

(21) Appl. No.: 10/516,184

(22) PCT Filed: Jun. 12, 2002

(86) PCT No.: PCT/JP02/05839

§ 371 (c)(1),
(2), (4) Date: Nov. 30, 2004

(87) PCT Pub. No.: WO03/105813

PCT Pub. Date: Dec. 24, 2003

(65) Prior Publication Data

US 2005/0240138 A1    Oct. 27, 2005

(51) Int. Cl.
*A61F 13/00* (2006.01)
*A61F 15/00* (2006.01)

(52) U.S. Cl. .............................. 602/57; 602/41; 602/42

(58) Field of Classification Search ................. 602/57, 602/41, 42, 58
See application file for complete search history.

(56) References Cited

U.S. PATENT DOCUMENTS 5,827,213 A * 10/1998 Jensen ........................ 602/62
6,018,092 A * 1/2000 Dunshee ...................... 602/54
6,093,465 A * 7/2000 Gilchrist et al. ........... 428/40.1
6,297,422 B1 * 10/2001 Hansen et al. ................ 602/57
6,911,571 B1 * 6/2005 Utsugi ......................... 602/58

FOREIGN PATENT DOCUMENTS

| EP | 1250922 A1 | * 10/2002 |
| JP | 10-182442 | * 10/1998 |
| JP | 2001-114672 | * 4/2001 |

OTHER PUBLICATIONS

Merriam-Webster OnLIne Dictionary; definition of "NOTCH", printed Mar. 27, 2006, 2 pages.*
MSN Encarta Dictionary; definition of "NOTCH", printed Mar. 27, 2006, 2 pages.*

* cited by examiner

Primary Examiner—Henry Bennett
Assistant Examiner—Kari Petrik
(74) Attorney, Agent, or Firm—Oliff & Berridge, PLC

(57) ABSTRACT

A liner for a patch used for covering the surface of a base agent layer of the patch may include a tear line portion for dividing and peeling the liner off the base agent layer is provided at a predetermined location. The thickness of the tear line portion may be made thinner than a generally average thickness of the liner. Therefore, when the patch is about to be used, the liner may easily be torn at the tear line portion and peeled off the base agent layer.

6 Claims, 2 Drawing Sheets

LINER FOR PATCH

TECHNICAL FIELD

The invention relates to a liner for a patch used for covering the surface of a basic agent layer of the patch.

BACKGROUND ART

With regard to patches, liners used for covering the surface of the base agent layer made of a tacky ointment or the like ordinarily have a thin film configuration made of various polymer materials. In most patches, the liner is integrated with the base agent layer as the liner is stuck to the surface of the base agent layer. When such a patch is about to be used, the liner is peeled off, generally by starting the peeling at a corner portion thereof, so as to expose the surface of the base agent layer.

Generally, the base agent layer is provided in a layer form on a flexible support, and such patches of various kinds, for example, poultices, plasters, tapes, etc., are commercialized. Therefore, it is important to facilitate the peeling of the liner off the base agent layer and therefore prevent the aforementioned patch from being deformed when the liner is peeled off.

Conventionally, in order to facilitate the peeling of the liner off the base agent layer of a patch, the use of a devised liner, for example, a liner that is provided with a linear or sawtooth tear line portion or that is divided into a plurality of pieces that can be peeled off one at a time, has been considered, and a variety of so devised liners have been proposed. The following examples of such liner constructions may be cited.

1) A liner construction wherein a central portion of a liner (peelable paper) covering the surface of a base agent layer provided on a support is provided with a wavy or sawtooth line of cuts that penetrate through the liner and align with intervals therebetween, so that the peeling of the liner can be started at the cut line portion (tear line portion) (Japanese Utility Model Publication No. HEI 5-4281).

2) A liner construction wherein a central portion of a liner covering the surface of a base agent layer is provided with linearly arranged perforations that penetrate through the liner, so that the perforated portion (tear line portion) will be torn and the liner will be peeled off by pulling the liner together with the base agent layer in the right and left directions (Japanese Patent Application Laid-Open Publication No. HEI 8-112305).

3) A liner construction wherein two liners cover the surface of a base agent layer and overlap each other at a central portion of the base agent layer, so that the peeling of the liners will be started at an overlap portion (a portion that is not in contact with the base agent layer) located at the central portion.

These liner constructions each have an arrangement of perforations or a line of cuts which penetrate through the liner, or have in a central portion thereof a line-shaped portion of overlap of two liners.

After a patch is produced, there is a possibility that, during storage or transportation of the patch, active ingredients and constituent ingredients of the base agent layer as well as the base agent layer itself may leak or seep out through an arrangement of perforations or a line of cuts which penetrate through the liner or a portion of overlap of two liners.

If an active ingredient or a constituent ingredient of the base agent layer leaks or seeps out or the base active layer itself leaks or seeps out, reduced effectiveness of the patch or degraded external appearance will result, and the usable life or the quality of the patch will deteriorate.

Therefore, if the base agent layer contains a volatile effective ingredient or constituent ingredient or a leachable effective ingredient or constituent ingredient that readily leaches out even through a small penetrating hole or if the base agent layer itself is leachable, no liner-penetrating hole is provided in the tear line portion of the liner. Furthermore, even if the tear line portion is provided with holes that penetrate through the liner (e.g., if the aforementioned volatility or leachability of an active ingredient or constituent ingredient is not very great, or if the leachability of the base agent layer itself is not very great), it is necessary to sufficiently consider properties of the holes that penetrate through the liner (e.g., the size of the holes, and the ratio of the entire length of the penetrating hole portions and the entire length of the tear line portion).

That is, if a liner is provided with holes that penetrate through the liner, the base agent layer contacts the outside through the penetrating holes, and therefore may suffer contamination from the external environment; therefore, it is preferable that the size and length of the penetrating holes be of minimum requirement.

However, in the conventional-art liners for patches, priority is given only to the facilitation of the peeling of the liner off the base agent layer. In a present circumstance, if the base agent layer contains a volatile effective ingredient or constituent ingredient or a leachable effective ingredient or constituent ingredient that readily leaches out even through a small penetrating hole or if the base agent layer itself is leachable, no sufficient consideration, besides the aforementioned priority, is given to prevention or restraint of the leaching of the aforementioned effective ingredient or constituent ingredient or the base agent layer, or to prevention of deterioration in the usable life and quality or degradation in the external appearance or reduction in the effectiveness of the patch during storage or transportation thereof.

Consequently, there is a demand for a liner for a patch which can easily and quickly be peeled off the base agent layer of the patch and which less tends to allow deterioration in the usable life and quality, degradation in the external appearance or reduction in the effectiveness of the patch during storage or transportation of the patch.

DISCLOSURE OF THE INVENTION

As a result of studies for solving the aforementioned problems of the conventional art, the inventors have found that if no hole penetrating through a liner is provided when the liner is provided with a tear line portion, the leakage or seepage of acting ingredients or constituent ingredients or the base agent layer itself through the liner can be avoided or sufficiently restrained, and that if a portion of the tear line portion of said liner is provided with a low-strength portion, the liner can easily be torn with the low-strength portion serving as a breach at the time of tear of the liner, and therefore have accomplished the invention.

Specifically, the liner for a patch of the invention is a liner for a patch used for covering a surface of a base agent layer of the patch, characterized in that a tear line portion for dividing and peeling the liner off said base agent layer is provided at a predetermined location in the liner, and that said tear line portion is a pressed portion whose thickness is formed thinner than the generally average thickness of said liner by pressing the liner in a direction of thickness with an edge portion of an edge portion-having pressing member (this construction will hereinafter be referred to as "i").

The following liners for a patch of the invention are preferable.

ii) The liner for a patch of i, wherein a ratio B/A of the thickness B of said tear line portion and the generally average thickness A of said liner is in a range of 1/100 to 99/100.

iii) The liner for a patch of i, wherein said tear line portion is provided in a central portion of said liner.

iv) The liner for a patch of i, wherein in the generally average thickness of said liner, a thickness of a central portion of said tear line portion is thinner than a thickness of an end portion of the tear line portion, or the thickness of the end portion of said tear line portion is thinner than the thickness of the central portion of the tear line portion The invention also relates to a patch comprising a support, a base agent layer, and a liner for a patch of the invention.

BEST MODES FOR CARRYING OUT THE INVENTION

Figure 1:
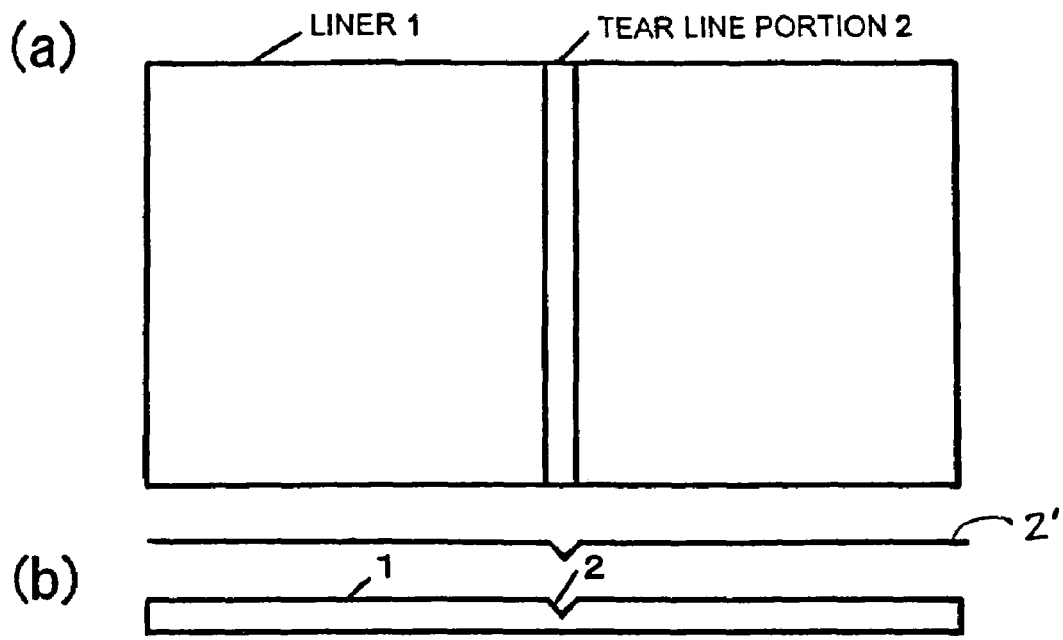
FIGS. 1(a) and 1(b) are front and end face views, respectively, showing a liner for a patch of the invention in Example 1.

Further description will be given hereinafter with respect to constituent elements of the liner for a patch of the invention and their functions.

a) With Regard to the Location to Provide a Tear Line Portion of a Liner and the Number of the Tear Line Portions and the Form Thereof a-1) With Regard to the Location to Provide a Tear Line Portion The location to provide a tear line portion of a liner is appropriately selected, taking into consideration the size, shape, purpose of use of the liner, etc. For example, if a rectangular liner is used, a tear line portion may be provided at a location that divides the liner at a suitable ratio, for example, 5:5 (1:1), 6:4, 7:3, etc., in the longitudinal direction or lateral direction. This division ratio is usually 1:1 (i.e., a tear line portion is provided in a central portion of the rectangular liner in the longitudinal direction or lateral direction). However, in the case of a liner having a special shape, for example, an extremely elongated rectangular liner, a tear line portion may be provided at the position of a division ratio of, for example, 8:2, 9:1, etc.

a-2) With Regard to the Number of Tear Line Portions

Ordinarily, the number of tear line portions may be one. If there is a need (e.g., in the case of a large liner or a liner elongated in the longitudinal direction or lateral direction), tear line portions may be provided at one or more location.

If a liner is provided with two or more tear line portions, tear line portions may be provided at two or more locations only in the longitudinal direction or the lateral direction; alternatively, tear line portions may also be provided, for example, at one location in the longitudinal direction (or lateral direction), and at one or more locations in the lateral direction (or longitudinal direction).

a-3) With Regard to the Form of Tear Line Portions

Although the shape of the tear line portion is preferably a linear shape, the shape thereof may be, for example, a wavy shape, a sawtooth shape, a rectangular wave shape, or a combination thereof, etc. if desired so.

The width of the tear line portion may be consistent throughout the entire tear line portion, or may be changed regularly or irregularly.

If the tear line portion is provided at one or more locations, the tear line portions may be provided in parallel with each other, or may be provided so as to cross each other, or may also be provided in, for example, a radial fashion, a concentric circle fashion, a branching fashion, etc., or may be provided in a combination thereof.

It is preferable that a tear line portion be continuously provided; however, it is also possible to provide tear line portions with intervals therebetween in accordance with circumstances.

The aforementioned forms of tear line portions may be used in an arbitrary combination.

b) With Regard to the Thickness of the Tear Line Portion

The thickness of the tear line portion is made thinner than a generally average thickness of the liner. In this case, the thickness may be consistent throughout the entire tear line portion, or the thickness of the tear line portion may be changed partly. If the thickness of a tear line portion is partly changed, it is appropriate that, for example, the thickness of a central portion of the tear line portion be made thinner than the thickness of an end portion of the tear line portion, or the thickness of an end portion of the tear line portion be made thinner than the thickness of a central portion of the tear line portion. This allows a tear initiation portion (breach) for tearing the liner at the tear line portion to be formed in a central portion or an end portion of the tear line portion.

c) With Regard to the Ratio B/A of the Thickness B of the Tear Line Portion and a Generally Average Thickness A of the Liner If the ratio B/A is excessively small, the liner will be torn, for example, even by a small force acting on the liner of the patch during storage or transportation of the patch. Conversely, if the ratio B/A is excessively large, it becomes difficult to tear the liner at the tear line portion. Therefore, considering these points, it is appropriate that the ratio B/A be in the rage of 1/100 to 99/100, and preferably 10/100 to 75/100, and most preferably 25/100 to 50/100.

d) With Regard to the Method for Making the Thickness of the Tear Line Portion Thinner than a Generally Average Thickness of the Liner As for the aforementioned method, it is possible to use a method in which the tear line portion is formed by pressing the liner in the direction of thickness with an edge portion of an edge portion-having pressing member.

Using an edge portion of a pressing member, the liner is pressed in the direction of thickness to a predetermined thickness. In this case, the tear line portion may be formed as a simple pressed portion that does not have a specific sectional shape, or a pressed portion having a specific sectional shape (e.g., a letter-V shape, a letter-U shape, a rectangular shape, a semicircular shape, a semielliptic shape, etc.) may be formed through the use of an edge portion having a specific edge shape.

e) With Regard to the Thickness of the Liner

In a generally average thickness of a liner, if the thickness of a central portion of a tear line portion is made thinner than the thickness of an end portion of the tear line portion, or if the thickness of an end portion of a tear line portion is made thinner than the thickness of a central portion of the tear line portion, provision of a cut line to a predetermined thickness, as for example, will still make the value of the aforementioned ratio B/A of the central portion of the tear line portion smaller than the value of B/A of the end portion thereof, or make the value of the aforementioned ratio B/A of the end portion of the tear line portion smaller than the value B/A of the central portion thereof, so that a tear initiation point (breach) can be formed in the central portion or the end portion of the tear line portion. As for means for making the thickness of a central portion of a tear line portion thinner than the thickness of an end portion of the tear line portion or making the thickness of an end portion of a tear line portion thinner than the thickness of a central portion of the tear line portion in a generally average thickness of the liner, it is possible to use conventional methods, for example, a method in which a central portion or an end portion of the liner is pressed, or the like. It is also possible to use a liner in which a generally average thickness of a central portion or an end portion thereof has been made thinner than a generally average thickness of the end portion or the central portion beforehand.

f) With Regard to the Method for Forming the Base Agent Layer

The base agent layer may be spread and applied on a liner, or may also be spread and applied on a suitable support.

g) With Regard to the Quality, Size and Shape of the Liner, the Base Agent Layer and the Support The liner, the base agent layer and the support can be produced or formed from materials normally used in the field of patches, so as to have a size and a shape that accord with purposes.

For example, a liner can be formed so as to have a predetermined size and a predetermined shape from a film made of polyethylene, polypropylene, polyester, polyvinyl chloride, cellulose, or a combination thereof, etc., which are appropriately selected in accordance with the purpose of use, taking into consideration properties of the liner, such as the water permeability, the air permeability, the flexibility, the thickness, etc. A surface of the liner may be coated with silicon in order to improve the peelability.

The base agent layer may be, for example, a layer made of an aqueous polymer or an ointment having tackiness and containing therein various active ingredients if so desired in accordance with purposes, and properties thereof, such as the thickness, the viscosity, etc., are appropriately selected.

The support may be, for example, a support made of a woven fabric or a nonwoven fabric made of natural fibers or synthetic fibers, or a polyester resin, a phenol resin, an epoxy resin, etc. A support that does not undergo either deformation or discoloration due to ingredients contained in the base agent layer is selected. Furthermore, since the patch needs to be pulled in order to divide the liner, it is preferable that the support be readily stretchable in association with the pulling of the patch, and it is appropriate to use a support that has stretchability in at least one direction.

EXAMPLES

Examples of the invention will be described below. Although in each example below, a tear line portion is provided at only one location in a central portion of a liner for convenience in description, it is naturally possible to provide tear line portion at two or more locations outside the central portion of the liner.

Example 1

FIG. 1 is drawings showing a liner for a patch of the invention in Example 1. FIG. 1(a) is a front view, and FIG. 1(b) is an end face view. In this example, a tear line portion 2 (a pressed portion having a letter-V groove shape) was formed in a liner 1 by pressing the liner 1 in the direction of thickness with a letter-V-shaped edge portion of an edge portion-having pressing member 2'. The sectional shape of the pressing portion may also be a rectangular groove, a letter-U groove, etc.

Example 2

Figure 2:
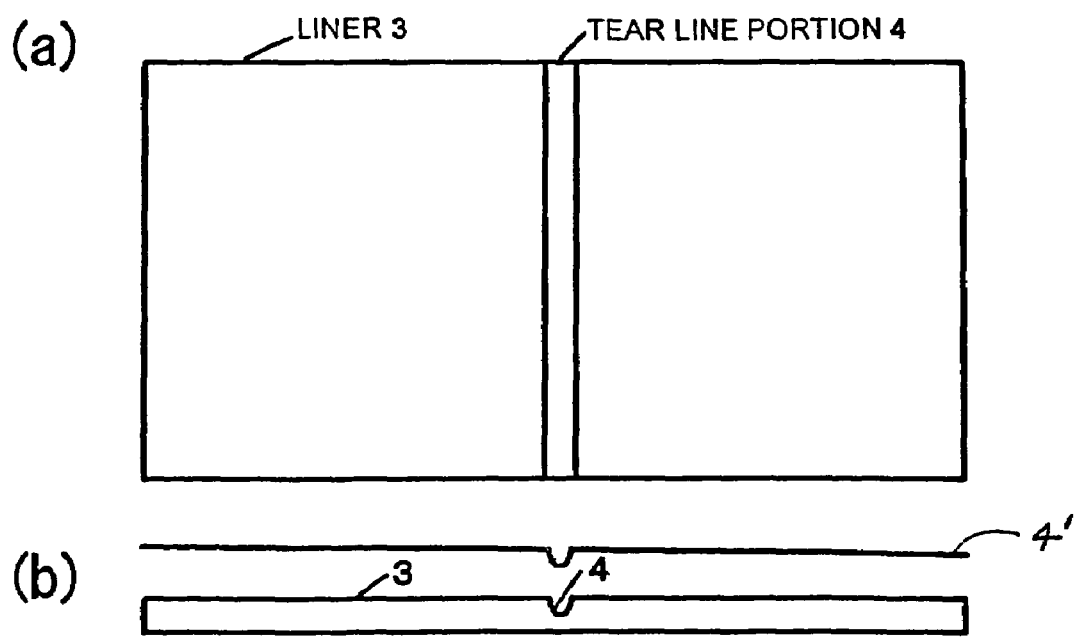
FIGS. 2(a) and 2(b) are front end and face views, respectively, showing a liner for a patch of the invention in Example 2.

FIG. 2 is drawings showing a liner for a patch of the invention in Example 2. FIG. 2(a) is a front view, and FIG. 2(b) is an end face view. In this example, a tear line portion 4 (a surface heat-treated portion having a letter-U groove shape) was provided in a liner 3 by pressing the liner 3 in the direction of thickness with a letter-U-shaped edge portion of an edge portion-having pressing member 4'. The sectional shape of the surface heat-treated portion is not particularly limited.

Example 3

Figure 3:
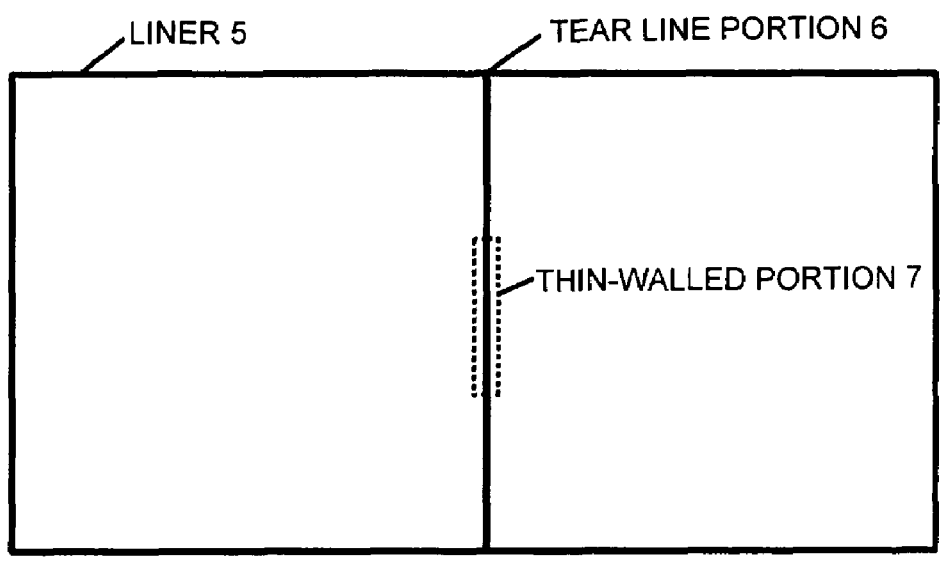
FIG. 3 is drawings showing a liner for a patch of the invention in Example 3.

FIG. 3 is a front view showing a liner for a patch of the invention in Example 3. In this example, a central portion of a tear line portion 6 (100 mm in length) of a liner 5 was provided with a thin-walled portion 7 where the thickness of the liner was made thinner than in other locations.

Example 4

Figure 4:
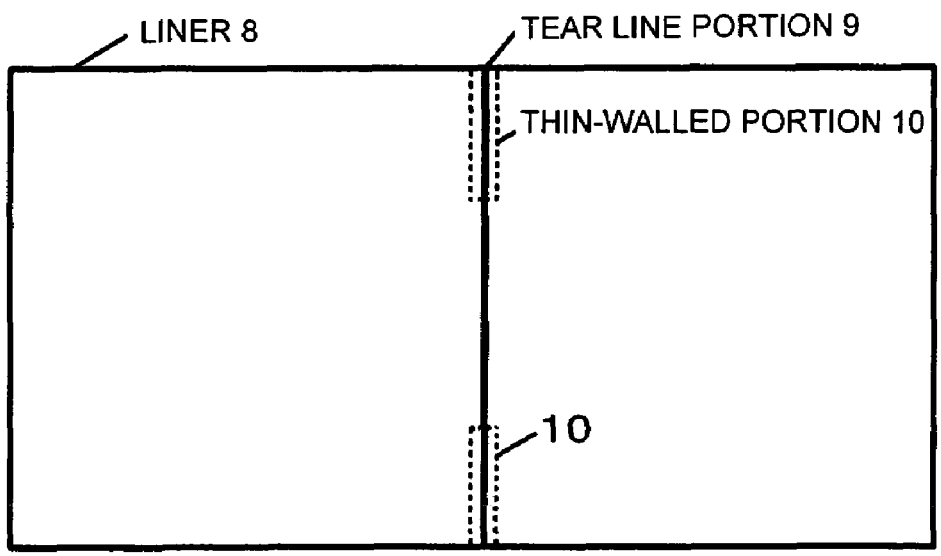
FIG. 4 is drawings showing a liner for a patch of the invention in Example 4.

FIG. 4 is a front view showing a liner for a patch of the invention in Example 4. In this example, vicinities of two end portions of a tear line portion 9 (100 mm in length) of a liner 8 were each provided with a thin-walled portion 10 where the thickness of the liner was made thinner than in other locations.

INDUSTRIAL APPLICABILITY

Since in the liner for a patch of the invention the thickness of the tear line portion is made thinner than a generally average thickness of the liner, the liner for a patch of the invention can easily be torn at the tear line portion and be peeled off the base agent layer when the patch of the invention employing the liner of the invention is used. Furthermore, since in the liner for a patch of the invention the tear strength of a portion of the tear line portion can be made lower than the tear strength of other portions thereof, the tear initiation location (breach) at the time of tear of the liner at the tear line portion can be formed at a desired location in the tear line portion of the liner.

Furthermore, since the liner for a patch of the invention can prevent or restrain the leaching of an acting ingredient or a constituent ingredient of the base agent layer or the base agent layer itself through the tear line portion, the liner of the invention is able to prevent deterioration in the usable life or quality, degradation in the external appearance, and reduction in the effectiveness of the patch of the invention employing the liner for a patch of the invention during storage or transportation thereof.

The invention claimed is:

1. A liner for a patch used for covering a surface of a base agent layer of the patch, comprising:
   a tear line portion for dividing and peeling the liner off said base agent layer provided at a predetermined location in the liner, said tear line portion comprising a pressed portion that defines an open width recess transverse to the tear line portion such that a thickness of the tear line portion at the recess is thinner than the generally average thickness of said liner.

2. The liner for a patch according to claim 1, wherein a ratio B/A of the thickness B of said tear line portion and the generally average thickness A of said liner is in a range of 1/100 to 99/100.

3. The liner for a patch according to claim 2, wherein said tear line portion is provided in a central portion of said liner.

4. The liner for a patch according to claim 1, wherein said tear line portion is provided in a central portion of said liner.

5. The liner for a patch according to claim 1, wherein, in the generally average thickness of said liner, a thickness of a central portion of said tear line portion is thinner than a thickness of an end portion of the tear line portion, or the thickness of the end portion of said tear line portion is thinner than the thickness of the central portion of the tear line portion.

6. A patch comprising a support, a base agent layer, and a liner for a patch according to claim 1.

* * * * *